(12) United States Patent
Tears et al.

(10) Patent No.: US 6,921,393 B2
(45) Date of Patent: Jul. 26, 2005

(54) ABSORBENT ARTICLE FOR ABSORBING BODY FLUIDS

(75) Inventors: Denise Crites Tears, Appleton, WI (US); Amanda Lee O'Connor, Neenah, WI (US); Russell Gerald Mayer, Appleton, WI (US); Stephen Alan Kolasinski, Appleton, WI (US); Wendy Jean Wegner, Appleton, WI (US); Chad Krueger, Neenah, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 577 days.

(21) Appl. No.: 10/080,888

(22) Filed: Feb. 22, 2002

(65) Prior Publication Data
US 2003/0163108 A1 Aug. 28, 2003

(51) Int. Cl.[7] .............................................. A61F 13/15
(52) U.S. Cl. .............................. 604/385.04; 604/385.28
(58) Field of Search ................... 604/385.04, 385.101, 604/385.28

(56) References Cited

U.S. PATENT DOCUMENTS

| | | |
|---|---|---|
| 2,064,431 A | 12/1936 | Jurgensen |
| 2,787,271 A | 4/1957 | Clark |
| 3,395,201 A | 7/1968 | Kalwaites |
| 3,411,504 A | 11/1968 | Glassman |
| 3,559,650 A | 2/1971 | Larson |
| 3,575,174 A | 4/1971 | Mogor |
| 3,635,221 A | 1/1972 | Champaigne |
| 3,886,941 A | 6/1975 | Duane et al. |
| 3,888,255 A | 6/1975 | Shah et al. |
| 4,059,114 A | 11/1977 | Richards |
| 4,204,532 A | 5/1980 | Lind et al. |
| 4,215,692 A | 8/1980 | Levesque |
| 4,324,245 A | 4/1982 | Mesek et al. |
| 4,589,876 A | 5/1986 | Van Tilburg |
| 4,627,847 A | 12/1986 | Puletti et al. |
| 4,655,759 A | 4/1987 | Romans-Hess et al. |
| 4,690,680 A | 9/1987 | Higgins |
| 4,692,161 A | 9/1987 | Puletti et al. |
| 4,718,898 A | 1/1988 | Puletti et al. |
| 4,770,657 A | 9/1988 | Ellis et al. |
| 4,773,904 A | 9/1988 | Nakanishi et al. |
| 4,834,739 A | 5/1989 | Linker, III et al. |
| 4,911,701 A | 3/1990 | Mavinkurve |
| 4,938,756 A | 7/1990 | Salek |
| 5,011,480 A | 4/1991 | Gossens et al. |
| 5,197,959 A | 3/1993 | Buell |
| 5,221,275 A | 6/1993 | Van Iten |
| 5,234,422 A | 8/1993 | Sneller et al. |
| 5,236,428 A | 8/1993 | Zajaczkowski |

(Continued)

FOREIGN PATENT DOCUMENTS

| | | |
|---|---|---|
| EP | 0 464 854 B1 | 8/1991 |
| EP | 0 687 453 A1 | 12/1995 |
| EP | 0 945 110 A2 | 9/1999 |
| FR | 2 423 171 | 11/1979 |
| GB | 2 233 235 A | 1/1991 |

*Primary Examiner*—Larry I. Schwartz
*Assistant Examiner*—C L Anderson
(74) *Attorney, Agent, or Firm*—Paul Y. Yee; Thomas J. Connelly (57) ABSTRACT

An absorbent article is disclosed having a liquid permeable bodyside cover, a liquid permeable garment side liner and an absorbent core enclosed by the cover and the liner. The absorbent article also has a pair of fringes formed by joining the cover to the liner. The pair of fringes extend laterally outward from the absorbent core and are capable of being biased upward to form a pair of upstanding side walls when placed in an undergarment. The pair of upstanding side walls form a pair of reservoirs located adjacent to the absorbent core. The pair of reservoirs are capable of retaining body fluid that has run off of the cover until the body fluid can be absorbed by the absorbent core.

22 Claims, 7 Drawing Sheets

U.S. PATENT DOCUMENTS

| | | |
|---|---|---|
| 5,300,058 A | 4/1994 | Goulait et al. |
| 5,312,386 A | 5/1994 | Correa et al. |
| 5,356,403 A | 10/1994 | Faulks et al. |
| 5,391,162 A | 2/1995 | Widlund et al. |
| 5,401,266 A | 3/1995 | Runeman et al. |
| 5,454,804 A | 10/1995 | Widlund |
| 5,489,283 A | 2/1996 | Van Tillburg |
| 5,516,567 A | 5/1996 | Roessler et al. |
| 5,624,423 A | 4/1997 | Anjur et al. |
| 5,649,917 A | 7/1997 | Roberts et al. |
| 5,704,928 A | 1/1998 | Morita et al. |
| 5,778,457 A | 7/1998 | Conway |
| H1746 H | 8/1998 | Carrier et al. |
| 5,795,344 A | 8/1998 | Chappell |
| 5,820,618 A | 10/1998 | Roberts et al. |
| 5,843,056 A | 12/1998 | Good et al. |
| 5,879,341 A | 3/1999 | Odorzynski et al. |
| 6,229,061 B1 | 5/2001 | Dragoo et al. |
| 6,371,948 B1 | 4/2002 | Mizutani |
| 6,689,113 B2 * | 2/2004 | Boulanger et al. ...... 604/385.04 |
| 2003/0116888 A1 | 6/2003 | Rymer et al. |
| 2003/0119402 A1 | 6/2003 | Melius et al. |

* cited by examiner

```
┌─────────────────────────────────────────────────────────┐
│ FORMING AN ABSORBENT ARTICLE HAVING AN ABSORBENT CORE   │
│ AND A PAIR OF FRINGES AND A RELEASABLE PEEL STRIP       │
│ COVERING A GARMENT ADHESIVE                             │
└─────────────────────────────────────────────────────────┘
                            │
┌─────────────────────────────────────────────────────────┐
│ POSITIONING A PRIMARY ABSORBENT UNDERGARMENT            │
│ HAVING A CROTCH PORTION ONTO A WEARER'S BODY            │
└─────────────────────────────────────────────────────────┘
                            │
┌─────────────────────────────────────────────────────────┐
│ REMOVING SAID PEEL STRIP FROM SAID ABSORBENT ARTICLE    │
└─────────────────────────────────────────────────────────┘
                            │
┌─────────────────────────────────────────────────────────┐
│ POSITIONING SAID ABSORBENT ARTICLE OVER SAID CROTCH     │
│ PORTION OF SAID PRIMARY ABSORBENT UNDERGARMENT          │
└─────────────────────────────────────────────────────────┘
                            │
┌─────────────────────────────────────────────────────────┐
│ PRESSING SAID ABSORBENT ARTICLE ONTO SAID PRIMARY       │
│ ABSORBENT UNDERGARMENT TO SECURE SAID GARMENT ADHESIVE  │
│ AND FORM A PAIR OF UPSTANDING SIDE WALLS FROM SAID PAIR │
│ OF FRINGES AND FORMING A PAIR OF RESERVOIRS ADJACENT TO │
│ SAID ABSORBENT CORE                                     │
└─────────────────────────────────────────────────────────┘
                            │
┌─────────────────────────────────────────────────────────┐
│ POSITIONING SAID PRIMARY ABSORBENT UNDERGARMENT AROUND  │
│ A WEARER'S TORSO WITH SAID PAIR OF UPSTANDING SIDE      │
│ WALLS ALIGNED IN THE WEARER'S GROIN                     │
└─────────────────────────────────────────────────────────┘
```

```
┌─────────────────────────────────────────────────────────────┐
│ FORMING AN ABSORBENT ARTICLE HAVING AN ABSORBENT CORE       │
│ AND A PAIR OF FRINGES AND A RELEASABLE PEEL STRIP           │
│ COVERING A GARMENT ADHESIVE                                 │
└─────────────────────────────────────────────────────────────┘
                              │
┌─────────────────────────────────────────────────────────────┐
│ POSITIONING A PRIMARY ABSORBENT UNDERGARMENT HAVING         │
│ A CROTCH PORTION ONTO A WEARER'S BODY                       │
└─────────────────────────────────────────────────────────────┘
                              │
┌─────────────────────────────────────────────────────────────┐
│ REMOVING SAID PEEL STRIP FROM SAID ABSORBENT ARTICLE        │
└─────────────────────────────────────────────────────────────┘
                              │
┌─────────────────────────────────────────────────────────────┐
│ POSITIONING SAID ABSORBENT ARTICLE OVER SAID CROTCH PORTION │
│ OF SAID PRIMARY ABSORBENT UNDERGARMENT                      │
└─────────────────────────────────────────────────────────────┘
                              │
┌─────────────────────────────────────────────────────────────┐
│ PRESSING SAID ABSORBENT ARTICLE ONTO SAID PRIMARY ABSORBENT │
│ UNDERGARMENT TO SECURE SAID GARMENT ADHESIVE AND FORM       │
│ A PAIR OF UPSTANDING SIDE WALLS FORM SAID OF FRINGES        │
│ AND FORMING A PAIR OF RESERVOIRS ADJACENT                   │
│ TO SAID ABSORBENT CORE                                      │
└─────────────────────────────────────────────────────────────┘
                              │
┌─────────────────────────────────────────────────────────────┐
│ POSITIONING SAID PRIMARY ABSORBENT UNDERGARMENT             │
│ AROUND A WEARER'S TORSO WITH SAID PAIR OF UPSTANDING        │
│ SIDE WALLS ALIGNED IN THE WEARER'S GROIN                    │
└─────────────────────────────────────────────────────────────┘
                              │
┌─────────────────────────────────────────────────────────────┐
│ LOWERING SAID PRIMARY ABSORBENT UNDERGARMENT AND            │
│ REMOVING SAID SOILED ABSORBENT ARTICLE                      │
└─────────────────────────────────────────────────────────────┘
```

ABSORBENT ARTICLE FOR ABSORBING BODY FLUIDS

BACKGROUND OF THE INVENTION

Today, many different forms of primary absorbent undergarments, diapers and fitted briefs are available to consumers who involuntarily expel urine or suffer from urinary incontinence. Some of these products are designed to resemble common cotton underwear except that they contain a highly absorbent material. Even though such products are relatively inexpensive, many people who use such products, especially the elderly, are interested in lower cost alternatives. One solution to this problem is to attach an inexpensive absorbent article, diaper insert or liner within the primary absorbent undergarment. When the absorbent article or liner is saturated with urine, it can easily be removed and discarded. Another absorbent article, diaper insert or liner can then be inserted into the primary absorbent undergarment so as to prolong the life of the primary absorbent undergarment. The absorbent article, diaper insert or liner is substantially less costly than the primary absorbent undergarment.

The absorbent article, diaper insert or liner differs in construction from current commercially available incontinence pads in that it exhibits the ability to allow urine and other body fluid to pass therethrough and enter the primary absorbent undergarment under controlled conditions.

Now an inexpensive absorbent article has been invented which is designed to allow body fluid to pass therethrough while prolonging the useful life of a primary absorbent undergarment.

SUMMARY OF THE INVENTION

Briefly, this invention relates to an absorbent article having a liquid permeable bodyside cover, a liquid permeable garment side liner and an absorbent core enclosed by the cover and the liner. The absorbent article also has a pair of fringes formed by joining the cover to the liner. The pair of fringes extend laterally outward from the absorbent core and are capable of being biased upward to form a pair of upstanding side walls when placed in an undergarment. The pair of upstanding side walls form a pair of reservoirs located adjacent to the absorbent core. The pair of reservoirs are capable of retaining body fluid that has run off of the cover until the body fluid can be absorbed by the absorbent core.

DETAILED DESCRIPTION

Figure 1:
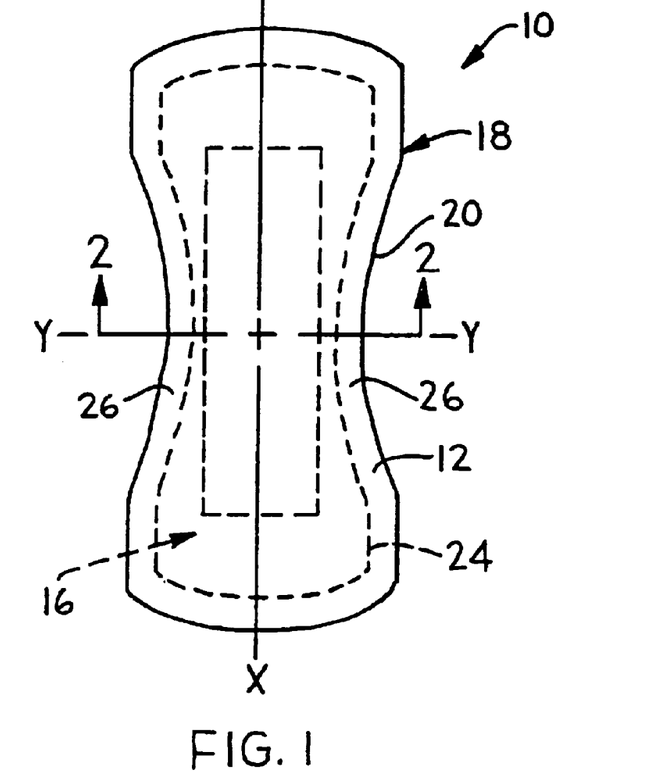
FIG. 1 is a top view of an absorbent article for urinary incontinence.
Figure 2:
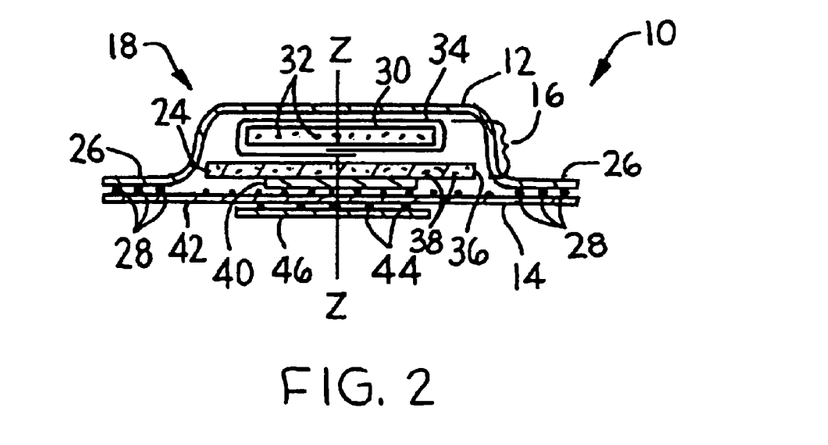
FIG. 2 is a cross-sectional view of the absorbent article shown in FIG. 1 taken along line 2—2.
Figure 3:
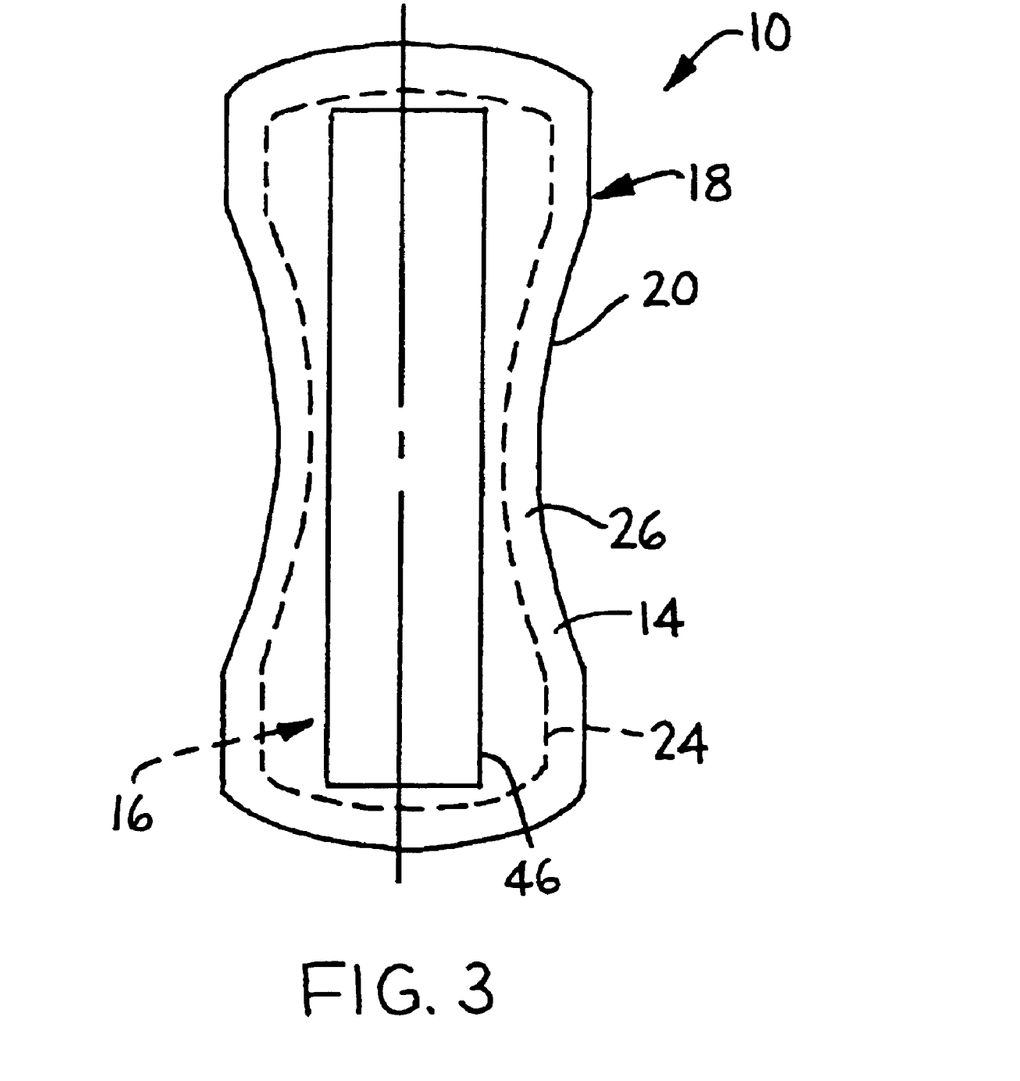
FIG. 3 is a bottom view of the absorbent article shown in FIG. 1.

Referring to FIGS. 1–3, an absorbent article 10, such as an incontinence pad capable of absorbing a relatively large quantity of urine, is shown constructed of a bodyside cover 12, a garment side liner 14 and an absorbent core 16. The bodyside cover 12 and the garment side liner 14 are both liquid permeable. By "liquid permeable" it is meant that body fluids, especially urine, and vapors can pass therethrough. The absorbent core 16 is enclosed by the liquid permeable bodyside cover 12 and the liquid permeable garment side liner 14 to form an absorbent pad 18 having a crotch portion 20. The absorbent article 10 is an elongated member having a longitudinal axis x—x, a transverse axis y—y and a vertical axis z—z. The absorbent article 10 can have a rectangular, hourglass, race track, oval, elliptical or other geometrical configuration when viewed from the top. The absorbent article 10 has a length, measured parallel to the longitudinal axis x—x, of less than about 500 millimeters (mm). Preferably, the absorbent article 10 has a length of less than about 400 mm, and most preferably, has a length of less than about 350 mm. The absorbent article 10 has a crotch width, measured parallel to the transverse axis y—y, of less than about 150 mm. Preferably, the crotch width of the absorbent article 10 is less than about 125 mm, and most preferably, the crotch width of the absorbent article 10 is less than about 110 mm. It should be noted that the absorbent article 10 could have a wider width when measured away from the crotch region. The absorbent article 10 also has a height, measured parallel to the vertical axis z—z, of from about 2 mm to about 25 mm. Preferably, the height of the absorbent article 10 is less than about 18 mm.

The liquid permeable cover 12 is designed to allow body fluid, particularly urine, to quickly pass therethrough and be received by the absorbent core 16. The bodyside cover 12 is placed in contact with the genital area of a human body. The bodyside cover 12 is capable of passing body fluid, voluntarily or involuntarily expelled from the urethra, downward into the absorbent core 16.

The liquid permeable cover 12 can be constructed from natural or synthetic material. The cover 12 can be formed from a woven or nonwoven material. Suitable materials include bonded carded webs of polyester, polypropylene, polyethylene, nylon or other heat-bondable fibers. Other polyolefins, such as copolymers of polypropylene and polyethylene, linear low-density polyethylene, finely perforated film webs and net materials also work well. A preferred material is spunbond. Spunbond is a nonwoven material formed from polypropylene fibers. Spunbond is sold commercially by Kimberly-Clark Corporation having an office at 401 North Lake Street, Neenah, Wis. 54956. The spunbond is treated to be hydrophilic so as to allow liquid to penetrate therethrough. The spunbond can contain from about 1% to about 2% titanium dioxide pigment to give it a clean, white appearance.

The bodyside cover 12 can be formed from a material having a variety of basis weights. When the bodyside cover 12 is formed from spunbond, the material should have a basis weight of from about 0.3 ounces per square yard (osy) to about 1.0 osy. Preferably, the basis weight for the spunbond material is from about 0.3 osy to about 0.5 osy. Most preferably, the basis weight of the spunbond material should be about 0.385 osy.

The liquid permeable bodyside cover 12 should allow body fluids, especially urine, that comes into contact with it to readily and quickly pass therethrough. In this regard, the material from which the cover 12 is constructed can be treated to be hydrophilic. Alternatively, the cover 12 can be constructed with pores or openings that permit liquids and/or gases to pass therethrough. The liquid permeability of the cover 12 can be measured using a common test procedure known to those skilled in the art.

The liquid permeable garment side liner 14, like the bodyside cover 12, is designed to allow body fluid, particularly urine, to pass quickly therethrough. The garment side liner 14 is designed to be positioned away from the human body. The garment side liner 14 is capable of allowing body fluid exiting from the absorbent core 16 to pass downward into a primary absorbent undergarment 22, see FIG. 4. The liquid permeable liner 14 can be constructed from natural or synthetic material. The liner 14 can be formed from a nonwoven material such as spunbond. The garment side liner 14 can be formed from a material having a variety of basis weights. When the garment side liner 14 is formed from spunbond, the material should have a basis weight of from about 0.3 ounces per square yard (osy) to about 1.0 osy. Preferably, the basis weight of the spunbond material is from about 0.3 osy to about 0.5 osy. Most preferably, the basis weight of the spunbond material should be about 0.385 osy.

The liquid permeable garment side liner 14 should allow body fluids that come into contact with it to readily and quickly pass therethrough. In this regard, the material from which the garment side liner 14 is constructed is treated to be hydrophilic. Alternatively, the garment side liner 14 can be constructed to have pores or openings that permit liquids and/or gases to pass through. It should be noted that the bodyside cover 12 and the garment side liner 14 can be formed from the same material. Preferably, both the bodyside cover 12 and the garment side liner 14 are formed from spunbond and both have a basis weight of 0.385 osy. The liquid permeability of the bodyside cover 12 and the garment side liner 14 can be equal to one another or be different from each other. Preferably, the liquid permeability of the bodyside cover 12 is equal to the liquid permeability of the garment side liner 14. When the liquid permeability is different the bodyside cover 12 and the garment side liner 14, the bodyside cover 12 should exhibit the higher liquid permeability. The reason for this is that the higher liquid permeability of the bodyside cover 12 will allow body fluid impinging thereon to pass quickly into the absorbent core 16 instead of pooling on the cover 12.

Referring still to FIGS. 1–3, the absorbent core 16 is shown having an outer periphery 24. The bodyside cover 12 and the garment side liner 14 are secured or attached to the absorbent core 16 so as to form a fringe 26. The fringe 26 extends laterally outward from the absorbent core 16. The fringe 26 can extend partially or completely around the outer periphery 24 of the absorbent core 16. The fringe 26 can be bifurcated or divided into a pair of fringes 26 each located on opposite sides of the crotch portion 20. Even when the fringe 26 extends 360 degrees around the absorbent core 16, it can be viewed as having two portions that form a pair of fringes 26 located adjacent to the crotch portion 20. The pair of fringes 26 extends along at least a portion of the length of the crotch portion 20. The pair of fringes 26 can be identical in size and shape and will have a predetermined width measured along the y—y axis. From here on, the absorbent article 10 will be described as having a pair of fringes 26.

The cover 12 and the liner 14 can be secured to the absorbent core 16 by an adhesive 28, which is preferably a construction adhesive. The construction adhesive 28 can be either a hot melt adhesive or a cold melt adhesive. A hot melt adhesive that works well is REXTAC® RT 2730. This construction adhesive is commercially available from Huntsman Polymers Corporation having a mailing address of P.O. Box 371263 Pittsburgh, Pa. 15251-7263. It should be noted that the construction adhesive 28 could also be present at other locations within the absorbent article 10. For example, the construction adhesive 28 can be present between the cover 12 and the underlying layer. The construction adhesive 28 can also be present between adjacent layers.

Other methods of securing the bodyside cover 12 to the garment side liner 14 are known to those skilled in the art. Examples of other attachment methods include: ultrasonic bonding, pressure bonds, heat bonds, heat and pressure bonds, and thermal bonds wherein one material is heated above its melting temperature and is bonded to a second material. The cover 12 and the liner 14 can also be secured together by using thread if desired. When the pair of fringes 26 are present in the crotch portion 20 of the absorbent article 10, they should extend for a distance of from about 1 inch (about 25.4 millimeters (mm)) to the entire length of the absorbent article 10. Preferably, the pair of fringes 26 will extend for a distance of at least 2 inches (about 51 mm). Most preferably, the pair of fringes 26 will extend for a distance of at least 3 inches (about 76 mm).

Referring now to FIG. 2, the absorbent core 16 can consist of one or more absorbent layers. The absorbent core 16 can be made from natural or synthetic fibers, including cellulose fibers, surfactant-treated meltblown fibers, wood pulp fibers, regenerated cellulose or cotton fibers, or coform. Coform is a blend of pulp and synthetic meltblown fibers. Two preferred absorbent materials are wood pulp fluff and coform.

In FIG. 2, the absorbent core 16 is shown made up of a first absorbent layer 30. The first absorbent layer 30 is positioned below the bodyside cover 12. The first absorbent layer 30 can optionally contain a hydrocolloidal material 32, commonly referred to as a superabsorbent. The superabsorbent can be a partially neutralized salt of polyacrylic acid.

A superabsorbent is normally added to the absorbent core 16 to increase the amount of fluid that the absorbent core 16 can absorb and retain. The fluid retention capacity, also referred to as fluid absorbent capacity, of the absorbent core 16, for urine, should be at least 150 grams (g). Preferably, the fluid absorbent capacity of the absorbent core 16 for urine is at least 200 g. Most preferably, the fluid absorbent capacity of the absorbent core 16 for urine is at least 250 g. It should be noted that saline is normally used in place of human urine when measuring the fluid retention or absorbent capacity of the absorbent core 16. Saline is an aqueous solution of about 0.9% sodium chloride by weight. One brand of saline is S/P® Certified Blood Saline, Saline is an aqueous solution of about 0.9% sodium chloride by weight. One brand of saline is S/P® Certified Blood Saline, which is commercially available from Baxter Diagnostics having an office in McGraw Park, Ill. The reason for using saline instead of actual human urine is that it is sanitary to handle in a laboratory. In addition, the absorbency results for an absorbent core tested using about 0.9% saline is very close to the absorbency results using human urine.

The superabsorbent 32 that can be added to the absorbent core 16 can be produced to have almost any physical form. Commonly, the superabsorbent 32 is in the shape of small particles having a major dimension of less than about 500 microns. Superabsorbents are commercially available from several different vendors including Dow Chemical Company, Hoechst-Celanese and Stockhausen Inc. Two superabsorbents that work well for retaining urine are DRYTECH® 2035M and FAVOR® SXM 880. DRYTECH® 2035M is available from Dow Chemical Company having a mailing address of P.O. Box 846028 Dallas, Tex. 75284-6028. FAVOR® SXM 880 is available from Stockhausen Inc. having a mailing address of P.O. Box 7247-7261 Philadelphia, Pa. 19170-7261.

It should also be noted that the absorbent core 16 could optionally be formed as a laminate structure with the superabsorbent 32 incorporated therein.

Returning to FIG. 2, the absorbent article 10 includes a tissue 34 that is C-folded around the first absorbent layer 30. The tissue 34 functions to retain the superabsorbent 32 therein. It is advantageous to utilize at least about 15 percent by weight of superabsorbent 32 in the first absorbent layer 30. Preferably, at least about 20 percent by weight of the superabsorbent 32 is present in the first absorbent layer 30. Most preferably, about 24 percent by weight of the superabsorbent 32 is present in the first absorbent layer 30. The use of this percentage by weight of the superabsorbent 32 will significantly increase both the fluid absorbing and the fluid retention capacity of the absorbent core 16.

It should be noted the superabsorbent 32 does not have to be present in the first absorbent layer 30. However, one must recognize that the absorbent capacity of the first absorbent layer 30 will be less if no superabsorbent is present. When one uses a concentration of superabsorbent in the first absorbent layer 30 in excess of about 15 percent by weight, it is advantageous to wrap the first absorbent layer 30 in the tissue 34 to prevent the fine superabsorbent particles from failing out. If no superabsorbent 32 is present or if the superabsorbent 32 represents less than about 15 percent by weight of the first absorbent layer 30, then the tissue 34 could be eliminated.

The absorbent core 16 also includes a second absorbent layer 36. The second absorbent layer 36 can also contain a hydrocolloidal material 38, commonly referred to as a superabsorbent. The superabsorbent 38 can be similar or different from the superabsorbent 32. However, from a cost and manufacturing standpoint, the superabsorbents 32 and 38 should be identical. The superabsorbent 38 can also be in particle form having a major dimension of less than about 500 microns. Such superabsorbents are commercially available from the vendors described above.

It has been found that the second or lower absorbent layer 36 can contain a lower, equal or greater percentage by weight of superabsorbent than the first absorbent layer 30. Preferably, the percentage by weight of the superabsorbent 38 in the second absorbent layer 36 will be less than the percentage by weight (excess of about 15 percent) of the superabsorbent 32 in the first absorbent layer 30. More preferably, the percentage by weight of the superabsorbent 38 in the second absorbent layer 36 will be less than about 12 percent by weight, most preferably, about 10 percent by weight. Since the percentage by weight of the superabsorbent 38 in the second absorbent layer 36 represents less than about 15 percent by weight of the second absorbent layer 36, it is not necessary to wrap the second absorbent layer 36 in tissue. As noted above with reference to the first absorbent layer 30, it is not necessary to include superabsorbent in the second absorbent layer 36. However, the absence of the superabsorbent 38 will decrease the fluid absorbent and the fluid retention capacity of the second absorbent layer 36.

It should be noted that even though the absorbent core 16 is described as including two absorbent layers 30 and 36, it could be formed from a single absorbent layer. Alternatively, the absorbent core 16 could be constructed of three or more absorbent layers, if desired.

Still referring to FIG. 2, an impediment layer 40 is positioned between the absorbent core 16 and the garment side liner 14. The impediment layer 40 is capable of slowing or blocking the downward movement of body fluid from the absorbent core 16 to the garment side liner 14. The impediment layer 40 acts as a barrier that prevents the body fluid from passing directly through it. Instead, the body fluid is forced to flow around the edges of the impediment layer 40 in order to contact the garment side liner 14. The impediment layer 40 can be formed from almost any type of liquid-impermeable material. A thermoplastic film is a good liquid-impermeable material that can be used to form the impediment layer 40. The thermoplastic film can be formed from polyethylene, polypropylene or a combination thereof. A polyethylene film having a thickness of less than about 2 mm works well.

It is also possible to form the impediment layer 40 from an adhesive, a polymer coating or from some other impervious material. For example, the adhesive or polymer coating could be sprayed or applied onto a portion of the lower surface of the second absorbent layer 36. By spraying or applying a thin adhesive or coating onto a portion of the second absorbent layer 36, an impediment layer 40 can be obtained. The adhesive or coating can be applied in liquid form such that a variety of impervious patterns or areas can be covered. The adhesive or coating can be self adhering and does not required another means for attaching it to the second absorbent layer 36. The adhesive or coating can be colored, if desired, to identify it from a non-coated surface. Desirably, the adhesive or coating is aligned along at least the central longitudinal portion of the liner 14. However, the pattern of adhesive or coating can take on almost any desired design, including multiple discrete shapes that are independently arranged over at least a portion of the exterior surface 42.

Still referring to FIG. 2, the absorbent core 16 has a height, measured parallel to the vertical axis z—z, of from about 2 mm to about 25 mm. Preferably, the absorbent core 16 has a height of from about 3 mm to about 20 mm. Most preferably, the absorbent core 16 has a height of from about 4 mm to about 15 mm. As the height of the absorbent core 16 increases, the fluid capacity of the absorbent core 16 normally increases. However, one should understand that the materials from which the absorbent core 16 is constructed, the presence of the superabsorbent 32 and/or 38, and the thickness of the absorbent core 16 will all determine the fluid capacity of the absorbent core 16. The height dimension is important for it can be used to determine the width dimension of the pair of fringes 26.

Each of the pair of fringes 26 has a width dimension, measured parallel to the transverse axis y—y, of from about 3 mm to about 30 mm. Preferably, each of the pair of fringes 26 has a width dimension of from about 5 mm to about 25 mm. Most preferably, each of the pair of fringes 26 has a width dimension of less than about 20 mm. The width of each of the pair of fringes 26 can be sized to be less than, equal to or be greater than the height of the absorbent core 16. Preferably, the width of each of the fringes 26 is sized to be equal to or be greater than the height of the absorbent core 16. Most preferably, the width of each of the fringes 26 is sized to be greater than the height of the absorbent core 16.

It should be noted that when the absorbent core 16 is constructed of more than one absorbent layer, the width of each of the pair of fringes 26 should be greater than the height of at least the lower absorbent layer.

Still referring to FIG. 2, the garment side liner 14 of the absorbent article 10 has an exterior surface 42. Secured to the exterior surface 42 is an attachment means 44. The attachment means 44 is preferably one or more strips of a garment adhesive. However, the attachment means 44 can include other forms of attachment mechanisms. Other forms of attachment mechanisms that can be utilized include hook and/or loop fasteners, tape, glue, etc. VELCRO® is one form of a hook fastener that engages a loop material. VELCRO® is a registered trademark of Velcro Industries having a mailing address of 406 Brown Avenue, Manchester, N.H. 03103. When the attachment means 44 is a garment adhesive, the adhesive can be either a hot or cold melt adhesive that is sprayed, brushed, slot coated or otherwise applied onto the exterior surface 42 of the liner 14. The garment adhesive can be applied as one or more beads, lines or strips of adhesive aligned approximately parallel to the longitudinal axis x—x. Preferably, the garment adhesive is a hot melt adhesive. Garment adhesive is commercially available from several vendors. One such vendor is National Starch Co. having an office at 10 Finderne Avenue, Bridgewater, N.J. 08807.

When a hook and loop fastener is used as the attachment means 44, the hook portion can be secured to a portion of the liner 14 and the loop portion can be secured to a portion of the primary absorbent undergarment 22 or vice versa. It should also be noted that some materials, like spunbond, can serve the same function as a loop material and therefore a separate patch of loop material does not have to be secured opposite to the hook material. For example, if a patch of hook material is secured to the liner 14, the primary absorbent undergarment 22 will not be required to have a patch of loop material secured to it.

As mentioned above, the liner 14 has an exterior surface 42 and a portion of this exterior surface 42 will contact the primary absorbent undergarment 22. The portion of the exterior surface 42 that will contact the primary absorbent undergarment 22 can be formed to have a high coefficient of friction making it a non-skid surface. For example, the exterior surface 42 can consist of a roughened surface, a treated surface or be made from a non-skid material. The roughened, treated or non-skid surface will provide a physical attachment to the primary absorbent undergarment 22. Another way of stating this is to say that the non-skid portion of the exterior surface 42 serves a similar function as the attachment means 44.

The attachment means 44 can be protected from contamination by a releasable or removable peel strip 46. The peel strip 46 is designed to be removed by the consumer just prior to positioning and attaching the absorbent article 10 to the crotch portion of the absorbent undergarment 22. The releasable peel strip 46 is generally slightly larger in overall dimensions when compared to the attachment means 44 so as to enable the absorbent article 10 to be manufactured at high speeds. By "high speeds" it is meant the ability to manufacture at a speed of more than 200 absorbent articles per minute. The peel strip 46 can be a white Kraft paper, coated on one side so that it can be easily released from the attachment means 44.

Figure 4:
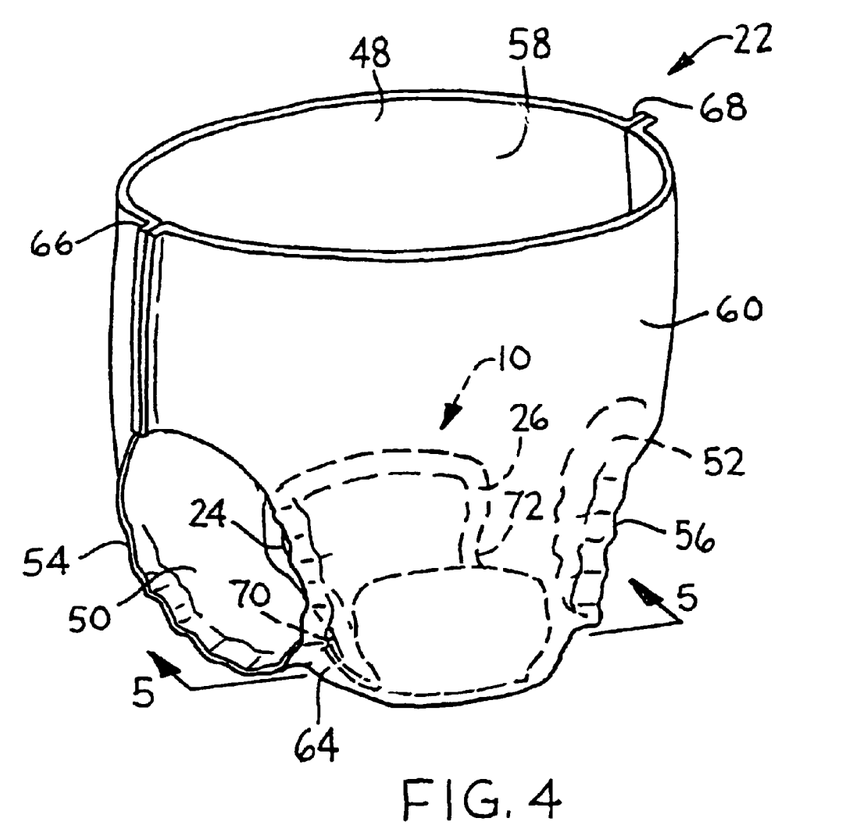
FIG. 4 is a perspective view of the absorbent article positioned in the crotch portion of an absorbent undergarment.
Figure 5:
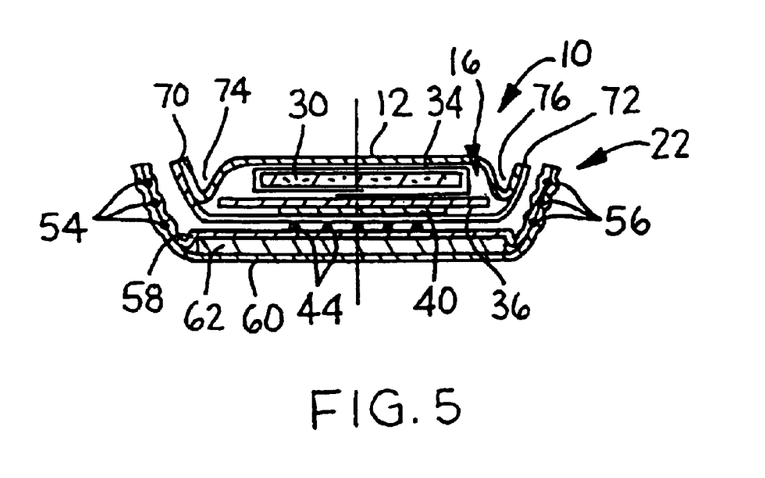
FIG. 5 is a cross-sectional view of the combination absorbent article and absorbent undergarment shown in FIG. 4 taken along line 5—5 and depicting the pair of upstanding side walls forming a pair of reservoirs positioned adjacent to the absorbent core.

Referring now to FIGS. 4 and 5, a primary absorbent undergarment 22 is shown having a waist opening 48 and a pair of leg openings 50 and 52. Each of the pair of leg openings 50 and 52 can be elasticized, if desired, by incorporating one or more strands of elastic, 54 and 56 respectively. The primary absorbent undergarment 22 also has a liquid permeable bodyside cover 58, a liquid-impermeable baffle 60, and an absorbent 62 positioned therebetween. Desirably, the absorbent 62 is completely enclosed between the cover 58 and the baffle 60. The bodyside cover 58 is designed to allow rapid intake of body fluid. The liquid permeable cover 58 can be constructed of a woven or nonwoven material formed from either natural or synthetic fibers that can easily be penetrated by body fluids. Suitable materials include bonded carded webs of polyester, polypropylene, polyethylene, nylon or other heat-bondable fibers. Other polyolefins, such as copolymers of polypropylene and polyethylene, linear low-density polyethylene, finely-perforated film webs and net materials, also work well.

The liquid-impermeable baffle 60 functions to prevent body fluid from passing therethrough. The liquid-impermeable baffle 60 can be made from a micro-embossed polymeric film, such as polyethylene or polypropylene, or it can be made from bicomponent films. A desired material is a polyethylene film having a thickness of less than about 3 mm. Composite materials formed from a polymer and a nonwoven fabric material can also be used. The composite sheets are generally formed by extrusion of the polymer onto a web of spunbond material to form an integral sheet. This material is desirable because the outer fabric surface is not irritating to the skin of the wearer and has a cushioned feel.

The primary absorbent undergarment 22 has a crotch portion 64 formed between the pair of leg openings, 50 and 52 respectively. The primary absorbent undergarment 22 is depicted as having a pair of side seams 66 and 68 that can be manually torn open. The undergarment 22 can be pulled up around the wearer's torso in a similar fashion as regular cotton underwear. For removal, the wearer can either pull the undergarment down away from the torso in a similar fashion as regular cotton underwear or one or both of the side seams 66 and 68 can be manually torn open for easy removal.

It should be noted that the primary absorbent undergarment 22 could be formed with a refastenable waist design such that the waist can be opened and closed more than once. Such a design is advantageous in allowing for tightening or loosening the primary absorbent undergarment 22 around the waist of the wearer.

The primary absorbent undergarment 22 can be in the form of a pant product, a brief product, an undergarment product, a reusable absorbent product, etc. These product descriptions are used by various manufacturers to identify differently configured absorbent products. The primary absorbent undergarment 22 is preferably a disposable product that will be discarded after a single use. However, the primary absorbent undergarment 22 could also be a disposable undergarment that is designed for multiple uses but typically is not to be laundered. Furthermore, the primary absorbent undergarment 22 can also be a non-disposable undergarment that can be laundered one or more times before being discarded. Still further, the primary absorbent undergarment 22 can be an undergarment that has a pocket or fold for containing a disposable insert or liner. Any and all such absorbent undergarments 22 are capable of being used in conjunction with the absorbent article 10.

The absorbent article 10 is designed to be attached to the bodyside cover 58 of the primary absorbent undergarment 22 by the attachment means 44. When attached, the crotch portion 20 of the absorbent pad 18 will cover or overlap at least a portion of the crotch portion 64 of the primary absorbent undergarment 22. Before the primary absorbent undergarment 22 is pulled up or fitted around the torso of the wearer, the absorbent article 10 can be secured to the bodyside cover 58. For example, the absorbent article 10 can be attached to the primary absorbent undergarment 22 before the primary absorbent undergarment 22 is placed on the wearer's body. Alternatively, the absorbent article 10 can be attached to the primary absorbent undergarment 22 when the undergarment 22 is positioned approximately about the shins, knees or thighs of the wearer. Still further, it is also possible for a caregiver to position the primary absorbent undergarment 22, in an open configuration, about the wearer's torso and then attach the absorbent article 10 before the primary absorbent undergarment 22 is closed and/or fastened around the wearer's waist.

As the absorbent article 10 is secured to the bodyside cover 58 of the primary absorbent undergarment 22, it acquires a cup shape configuration due to the cup shape configuration or curvature of the primary absorbent undergarment 22. This cup shape configuration causes the pair of fringes 26 to be biased upward and form a pair of upstanding side walls 70 and 72. Each of the pair of fringes 26 and therefore the pair of side walls 70 and 72 are free of elastics. It is not necessary that stretchable material or material that can extend or contract in at least one direction be present in the pair of fringes 26 in order to make the pair of side walls 70 and 72 stand upright. The combination of the curvature of the primary absorbent undergarment 22 and the width dimension of the pair of fringes 26 will allow the pair of side walls 70 and 72 to acquire an upright orientation.

Turning now to FIG. 5, the pair of upstanding side walls 70 and 72 forms a pair of reservoirs 74 and 76. Each of the reservoirs 74 and 76 is located adjacent to and outward from a side edge of the absorbent core 16. The pair of reservoirs 74 and 76 are capable of retaining body fluid that may run off or that has run off of the bodyside cover 12 until the body fluid can be absorbed by the absorbent core 16. The construction of the absorbent article 10 and the width dimension of the pair of fringes 26 dictate the depth of each of the pair of reservoirs 74 and 76. The pair of fringes 26 can be sized to be equal to or be greater than the height of the absorbent core 16. In this design, one can be assured that the pair of side walls 70 and 72 will have sufficient height to hold body fluid that may have pooled on the bodyside cover 12 and has run laterally off to one or both sides. The pair of reservoirs 74 and 76 should also have a length that extends at least the length of the crotch portion 20 of the absorbent pad 18. Preferably, each of the pair of reservoirs 74 and 76 will have a length of greater than about 1 inch (about 25.4 mm). More preferably, each of the pair of reservoirs 74 and 76 will have a length of greater than about 2 inches (about 51 mm). Most preferably, each of the pair of reservoirs 74 and 76 will have a length of greater than about 3 inches (about 76 mm).

The absorbent article 10 can be visualized as a secondary absorbent structure that is used to extend or prolong the useful life of the primary absorbent undergarment 22. Since the primary absorbent undergarment 22 is more costly than the absorbent article 10, the consumer can extend the life of the primary absorbent article 22 for a relatively small amount of money. It is also possible for the consumer to sequentially exchange the original absorbent article 10 with one or more absorbent article 10 before the primary absorbent undergarment 22 becomes so saturated with body fluid that it has to be replaced.

It should be noted that the purpose of the absorbent article 10 is to receive and retain body fluid, especially urine. The absorbent article 10 is constructed with a liquid permeable cover 12 and a liquid permeable liner 14 so as to permit excess body fluid to pass quickly down into the primary absorbent undergarment 22. However, if the absorbent article 10 is insulted with body fluid at a slow rate, the absorbent article 10 may be able to absorb and retain essentially all of the body fluid expelled from the user. In this situation, the wearer can remove the saturated absorbent article 10 and replace it with another dry absorbent article 10. This action will allow the primary absorbent undergarment 22 to stay dry and be used over an extended period of time.

Method of Using the Absorbent Article

Referring to FIGS. 6–9, various methods of securing the absorbent article 10 to a primary absorbent undergarment 22, positioning the undergarment 22 around a wearer's torso, replacing the absorbent article 10 and/or removing the primary absorbent undergarment 22 from the wearer's body are depicted. Starting with the flow diagram shown in FIG. 6, the absorbent article 10 functions to prolong the life of a primary absorbent undergarment 22. The undergarment 22 has a liquid permeable bodyside cover 58, a liquid-impermeable baffle 60 and an absorbent 62 positioned between the cover 58 and the baffle 60. The primary absorbent undergarment 22 also has a waist opening 48, a pair of leg openings 50 and 52 and a crotch portion 64 formed between said pair of leg openings 50 and 52. The method includes releasably attaching the absorbent article 10 to the primary absorbent undergarment. The absorbent article 10 is specially constructed to allow body fluid, especially urine, to pass completely therethrough fairly rapidly.

Figure 6:
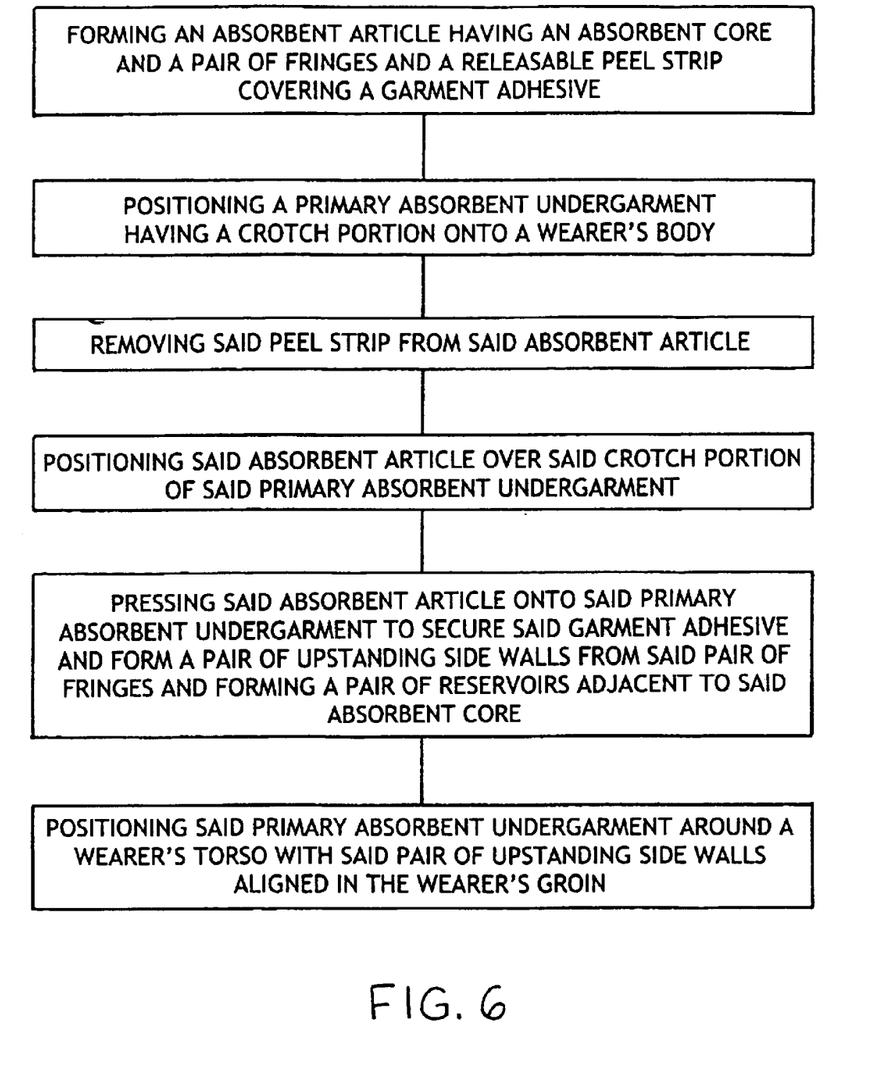
FIG. 6 is a flow diagram depicting a method of positioning an undergarment onto a wearer's legs and securing an absorbent article to the undergarment before pulling the undergarment up around a wearer's torso.

The absorbent article 10 has a liquid permeable bodyside cover 12 and a liquid permeable garment side liner 14. Preferably, the liquid permeable bodyside cover 12 and the liquid permeable garment side liner 14 will both have the same liquid permeability. The liner 14 has an exterior surface 42 with an attachment means 44 secured thereto. A releasable peel strip 46 covers the attachment means 44 to protect it from contamination prior to use of the absorbent article 10 by the consumer. The absorbent article 10 also includes an absorbent core 16 enclosed by the bodyside cover 12 and the garment side liner 14. The absorbent article 10 further has a pair of fringes 26 formed by joining the bodyside cover 12 to the garment side liner 14. The pair of fringes 26 extend laterally outward from the absorbent core 16. The pair of fringes 26 do not contain any elastic treads or elastic strands. In other words, the pair of fringes 26 are free of elastic.

The consumer can position the primary absorbent undergarment 22 onto his or her body by pulling the primary absorbent undergarment 22 up over their legs in the same manner as conventional underwear is applied. Alternatively, if the primary absorbent undergarment 22 has a refastenable waist, the waist can be opened and the undergarment 22 can be positioned around the torso of the wearer before the waist is again closed. Most commonly, the wearer will step into the waist opening 48 and place a leg through each of the leg openings 50 and 52. The primary absorbent undergarment 22 is then raised or pulled upward from the ankles, along the shins, past the knees and to the thighs. Somewhere between the ankles and the thighs, the wearer can laterally move his or her legs apart so as to cause the crotch portion 64 to be stretched out. At this point, the waist opening 48 is still below the wearer's torso and waist. Preferably, the waist opening 48 is positioned about even with or below the wearer's thighs before the absorbent article 10 is placed over at least a portion of the crotch portion 64. The crotch portion 64 of the primary absorbent undergarment 22 will exhibit a cup shape configuration or curvature due to the construction of the primary absorbent undergarment 22.

At this time, the wearer removes the releasable peel strip 46 from the absorbent article 10 and this exposes the attachment means 44. The wearer then centers or aligns the crotch portion 20 of the absorbent article 10 over at least a portion of the crotch portion 64 of the primary absorbent undergarment 22. The wearer then presses the absorbent article 10 against the crotch portion 64 of the primary absorbent undergarment 22 to secure the attachment means 44 thereto. Preferably, the consumer will firmly press the absorbent article 10 onto the crotch portion 64 of the primary absorbent undergarment 22. At this time; the waist opening 48 of the primary absorbent undergarment 22 is still positioned about even with or below the wearer's thighs. The primary absorbent undergarment 22 can then be pulled up along the thighs of the wearer or, if the primary absorbent undergarment 22 is of a refastenable design, it can be secured around the torso of the wearer. Alternatively, the wearer may place the absorbent article 10 in the area of the primary absorbent undergarment 22 where it is most likely to be insulted by body fluid.

Figure 7:
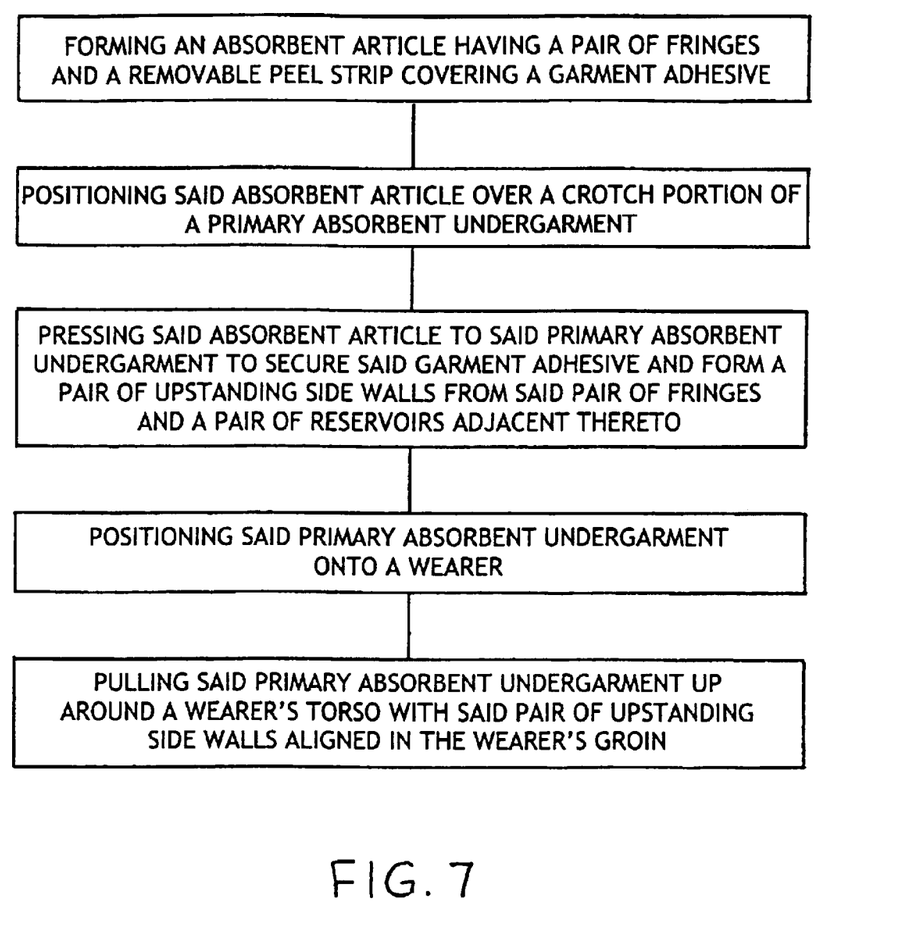
FIG. 7 is a flow diagram depicting a method of securing an absorbent article to an undergarment and positioning the undergarment around a wearer's torso.

Referring to FIG. 7, it should be noted that the consumer could also secure the absorbent article 10 to at least a portion of the crotch portion 64 of the primary absorbent undergarment 22 before the primary absorbent undergarment 22 is placed on his or her body. In this case, the wearer will remove the releasable peel strip 46 from the absorbent article 10 and expose the attachment means 44. The wearer then places or aligns the crotch portion 20 of the absorbent article 10 over at least a portion of the crotch portion 64 of the primary absorbent undergarment 22. The wearer then presses the absorbent article 10 against the crotch portion 64 of the primary absorbent undergarment 22 to secure the attachment means 44 thereto. The primary absorbent undergarment 22 can then be pulled up over the legs and thighs of the wearer or, if the primary absorbent undergarment 22 is of a refastenable design, it can be secured around the torso of the wearer. Alternatively, the wearer may place the absorbent article 10 in the area of the primary absorbent undergarment 22 where it is most likely to be insulted by body fluid.

In both methods depicted in FIGS. 6 and 7, the absorbent article 10 will acquire a cup shape configuration matching the crotch portion 64 of the primary absorbent undergarment 22. This causes the pair of fringes 26 to be biased upward and form a pair of upstanding side walls 70 and 72. The pair of upstanding side walls 70 and 72 forms a pair of reservoirs 74 and 76 adjacent to the absorbent core 16. The pair of reservoirs 74 and 76 are capable of retaining body fluid that has run off of the bodyside cover 12 until the body fluid can be absorbed by the absorbent core 16.

The wearer can pull up and position the primary absorbent undergarment 22 around his or her torso such that the pair of upstanding side walls 70 and 72 are aligned in the wearer's groin. The pair of upstanding side walls 70 and 72 will assist in preventing side leakage of body fluid from the absorbent article 10.

Figure 8:
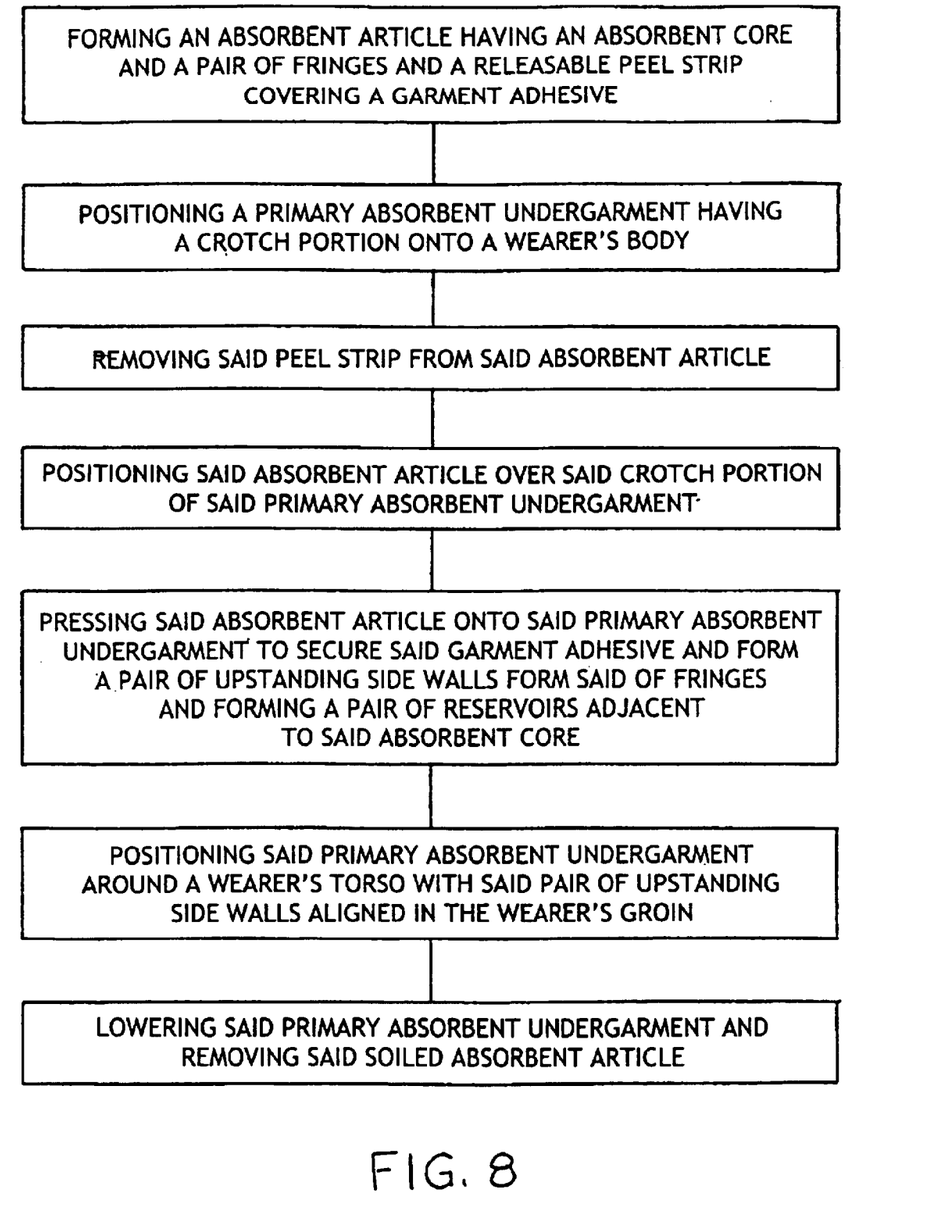
FIG. 8 is a flow diagram depicting a method of securing an absorbent article to an undergarment, positioning the undergarment around a wearer's torso and then removing the soiled absorbent article.

Referring to FIG. 8, one of the unique aspects of the absorbent article 10 is that it can absorb and pass body fluid, especially urine, down into the primary absorbent undergarment 22. However, since the absorbent article 10 contains superabsorbent 32, it has the ability to also retain body fluid for a certain period of time. The exact time period will depend upon how the absorbent article 10 is insulted with body fluid and how much body fluid is deposited thereon. For example, a slow dribble of body fluid onto the absorbent article 10 will be easily absorbed and retained. A rapid gush of a large quantity of body fluid would most likely mean that some of the body fluid would pass down into the primary absorbent undergarment 22.

The ability of the absorbent article 10 to both retain and pass body fluid means that the wearer may have the option to replace the absorbent article 10 once it becomes wetted or saturated with body fluid but before the primary absorbent undergarment 22 is saturated. By removing the saturated absorbent article 10 and sequentially replacing it with a second absorbent article 10, the wearer can substantially extend and prolong the life of the primary absorbent undergarment 22. It is possible in some instances that the initial absorbent article 10 can be removed and replaced multiple times before the primary absorbent undergarment 22 has to be discarded.

The absorbent article 10 will increase in weight as it acquires body fluid. The absorbent article 10 might also become damp or wet to the wearer as more and more body fluid is absorbed by the absorbent article 10. These conditions will indicate to the wearer that it is time to replace the absorbent article 10. Some wearers will also become accustomed to their body fluid discharge rate and therefore will tend to replace the absorbent article 10 at set time intervals. Either way, the wearer can easily and discretely change the absorbent article 10 without taking off their slacks, pants, etc. The absorbent article 10 can be removed or withdrawn by first lowering the primary absorbent undergarment 22 from around the wearer's torso. The primary absorbent undergarment 22 can be lowered to the wearer's thighs, knees, shins or ankles, whatever distance is comfortable to the wearer. The saturated absorbent article 10 is then removed by pulling up on the absorbent article 10 to release the attachment means 44. Although not shown in FIG. 8, at this point the soiled absorbent article 10 can be discarded in a trash container and a new or second absorbent article 10 can be attached to the primary absorbent undergarment 22 using the same procedure explained above for the initial absorbent article 10. The primary absorbent undergarment 22 is then pulled up around the wearer's torso and the second absorbent article 10 can be positioned adjacent to the wearer's groin.

Figure 9:
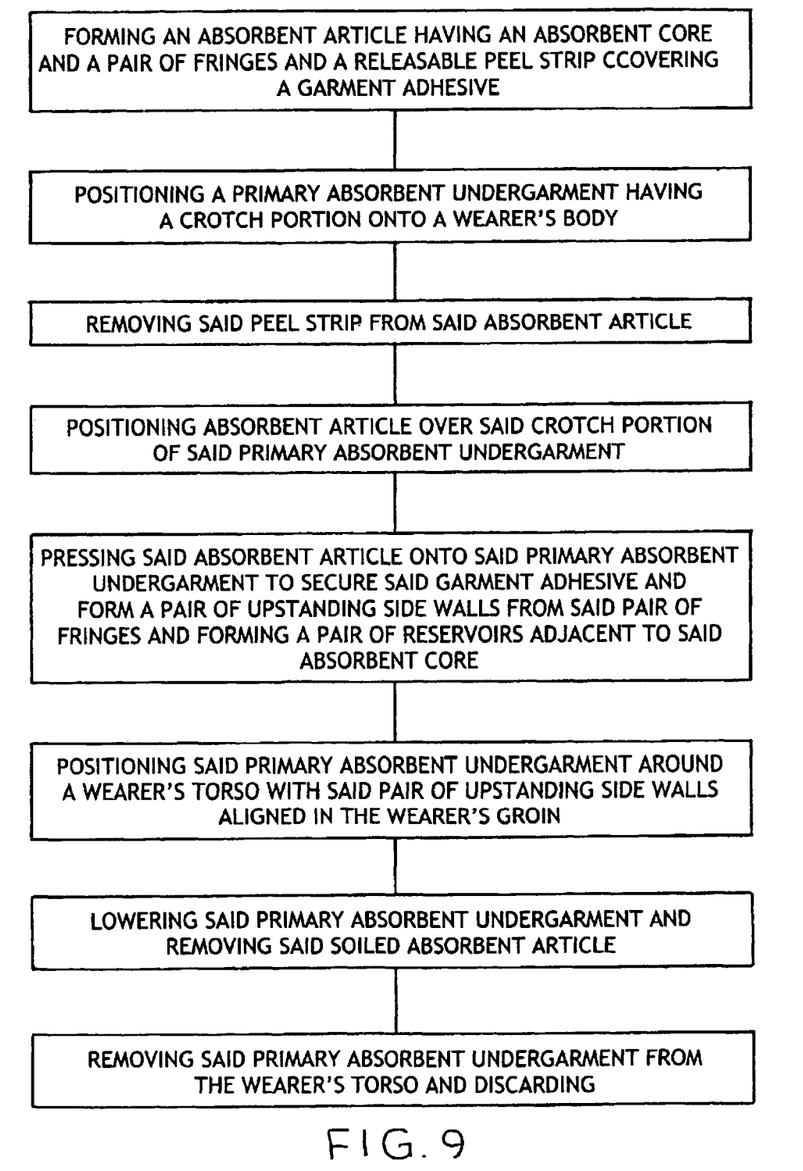
FIG. 9 is a flow diagram depicting a method of securing an absorbent article to an undergarment, positioning the undergarment around a wearer's torso and then removing the undergarment from the wearer's torso and discarding.

Referring now to FIG. 9, the absorbent article 10 and the primary absorbent undergarment 22 can both be removed from the wearer's torso or body after they have become soiled or saturated. Each can be removed individually or both can be removed simultaneously. Both can be removed simultaneously by pulling the primary absorbent undergarment 22 downward away from the wearer's torso and sliding the undergarment 22 off of the wearer's legs. The two absorbent articles 10 and 22 can then be discarded in a trash container. Alternatively, if the primary absorbent undergarment 22 has manually tearable side seams 66 and 68, see FIG. 4, one or both of the side seams 66 and 68 can be opened. This action will allow the primary absorbent undergarment 22 to be removed from the wearer's body without having to slide it down the wearer's legs. The tear open feature is beneficial for older people who may suffer from dexterity problems. The tear open feature can also assist a caregiver that may be tending to an elderly patient or an immobile patient.

It should be noted that it is possible to use two or more absorbent articles 10 in the primary absorbent undergarment 22 at the same time. Preferably, one absorbent article 10 will be aligned vertically above the second absorbent article 10. By using two or more absorbent articles 10 at the same time, one can further extend or prolong the life of the primary absorbent undergarment 22. When the upper most absorbent article 10 becomes saturated with body fluid, it can be removed. It is possible to replace the upper most absorbent article 10 at this time with a new dry absorbent article 10, if desired.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations that fall within the spirit and scope of the appended claims.

We claim:

1. An absorbent article comprising:
   a) a liquid permeable bodyside cover;
   b) a liquid permeable garment side liner;
   c) an absorbent core enclosed by said cover and said liner; and
   d) a pair of fringes formed by joining said cover to said liner which extend laterally outward from said absorbent article, said pair of fringes capable of being biased upward to form a pair of upstanding side walls when placed in an undergarment, said pair of upstanding side walls forming a pair of reservoirs located adjacent to said absorbent core, said pair of reservoirs being capable of retaining body fluid that has run off of said bodyside cover until said body fluid can be absorbed by said absorbent core;
   wherein said liquid permeable bodyside cover has a predetermined liquid permeability and said liquid permeable garment side liner has a liquid permeability equal to that of said liquid permeability of said bodyside cover.

2. The absorbent article of claim 1 wherein said bodyside cover and said garment side liner are formed from the same material.

3. The absorbent article of claim 2 wherein said bodyside cover is spunbond.

4. The absorbent article of claim 3 wherein said spunbond has a basis weight of from about 0.3 osy to about 1.0 osy.

5. The absorbent article of claim 1 wherein said garment side liner is spunbond.

6. The absorbent article of claim 5 wherein said spunbond has a basis weight of from about 0.3 osy to about 1.0 osy.

7. The absorbent article of claim 1 further comprising an impediment layer positioned between said absorbent core and said garment side liner, said impediment layer capable of slowing the downward movement of body fluid from said absorbent core to said garment side liner.

8. The absorbent article of claim 7 wherein said impediment layer is formed from an adhesive.

9. An absorbent article comprising:
   a) a liquid permeable bodyside cover having a predetermined liquid permeability;
   b) a liquid permeable garment side liner having an exterior surface with an attachment means secured thereto, said attachment means designed to be adhered to a primary absorbent undergarment, and said liner having a liquid permeability equal to said liquid permeability of said bodyside cover;
   c) an absorbent core enclosed by said cover and said liner; and
   d) a pair of fringes formed by joining said cover to said liner which extend laterally outward from said absorbent article, said pair of fringes capable of being biased upward to form a pair of upstanding side walls when placed in an undergarment, said pair of upstanding side walls forming a pair of reservoirs located adjacent to said absorbent core, said pair of reservoirs being capable of retaining body fluid that has run off of said bodyside cover until said body fluid can be absorbed by said absorbent core.

10. The absorbent article of claim 9 further comprising an impediment layer positioned between said absorbent core and said garment side liner, said impediment layer capable of slowing the downward movement of body fluid from said absorbent core to said garment side liner.

11. The absorbent article of claim 9 wherein said absorbent core has an outer periphery and said pair of fringes extends partially along said outer periphery.

12. The absorbent article of claim 11 wherein said absorbent core has a predetermined height and each of said pair of fringes has a width dimension that is greater than the height of said absorbent core.

13. The absorbent article of claim 9 wherein said pair of upstanding side walls are free of elastics.

14. The absorbent article of claim 9 wherein each of said pair of fringes has a width dimension that ranges from about 5 mm to about 25 mm.

15. The absorbent article of claim 9 wherein said absorbent article is secured to said undergarment by a hook fastener.

16. An absorbent article comprising:
   a) a liquid permeable bodyside cover having a predetermined liquid permeability;
   b) a liquid permeable garment side liner having an exterior surface with a garment adhesive secured thereto, said garment adhesive designed to be adhered to a primary absorbent undergarment, and said liner having a liquid permeability equal to said liquid permeability of said bodyside cover;
   c) an absorbent core enclosed by said cover and said liner to form an absorbent pad having a crotch portion; and
   d) a pair of fringes formed by joining said cover to said liner which extend laterally outward from said absorbent core, said pair of fringes capable of being biased upward at least in said crotch portion to form a pair of upstanding side walls when placed in an undergarment, said pair of upstanding side walls forming a pair of reservoirs located adjacent to said absorbent core, said pair of reservoirs being capable of retaining body fluid that has run off of said bodyside cover until said body fluid can be absorbed by said absorbent core.

17. The absorbent article of claim 16 further comprising an impediment layer positioned between said absorbent core and said garment side liner, said impediment layer capable of slowing the downward movement of body fluid from said absorbent core to said garment side liner.

18. The absorbent article of claim 17 wherein said impediment layer is formed from an adhesive.

19. The absorbent article of claim 16 wherein said liner has an exterior surface and a portion of said exterior surface has a non-skid surface that contacts said undergarment.

20. The absorbent article of claim 16 wherein said absorbent article has a crotch width dimension that is less than about 150 mm.

21. The absorbent article of claim 20 wherein said absorbent article has a crotch width dimension that is less than about 110 mm.

22. The absorbent article of claim 16 wherein said absorbent core includes at least two absorbent layers.

* * * * *